United States Patent

Platzek et al.

Patent Number: 5,690,909
Date of Patent: Nov. 25, 1997

[54] FLUORINE-CONTAINING MACROCYCLIC METAL COMPLEXES

[75] Inventors: Johannes Platzek; Bernd Radüchel; Ulrich Niedballa; Hanns-Joachim Weinmann; Hans Bauer; Klaus Roth, all of Berlin, Germany

[73] Assignee: Schering Aktiengesellschaft, Berlin, Germany

[21] Appl. No.: 553,432

[22] PCT Filed: Apr. 29, 1994

[86] PCT No.: PCT/EP94/01377

§ 371 Date: Mar. 19, 1996

§ 102(e) Date: Mar. 19, 1996

[87] PCT Pub. No.: WO94/27978

PCT Pub. Date: Dec. 8, 1994

[30] Foreign Application Priority Data

May 24, 1993 [DE] Germany .................... 43 17 588.0

[51] Int. Cl.$^6$ ............................................... A61K 49/00
[52] U.S. Cl. .................................. 424/9.363; 540/452
[58] Field of Search ...................... 540/452; 424/9.363

[56] References Cited

U.S. PATENT DOCUMENTS

| | | | |
|---|---|---|---|
| 4,885,363 | 12/1989 | Tweedle et al | 540/465 |
| 5,386,028 | 1/1995 | Tilstam et al. | 540/474 |

FOREIGN PATENT DOCUMENTS

| | | |
|---|---|---|
| 0255471 | 2/1988 | European Pat. Off. . |
| 0292689 | 11/1988 | European Pat. Off. . |
| 0299795 | 1/1989 | European Pat. Off. . |
| 0434345 | 6/1991 | European Pat. Off. . |
| 0434346 | 6/1991 | European Pat. Off. . |
| 0448191 | 9/1991 | European Pat. Off. . |
| 0485045 | 5/1992 | European Pat. Off. . |
| 0512661 | 11/1992 | European Pat. Off. . |
| 9324469 | 12/1993 | WIPO . |

*Primary Examiner*—Mukund J. Shah
*Assistant Examiner*—Michael Bucknum
*Attorney, Agent, or Firm*—Millen, White, Zelano, & Branigan, P.C.

[57] ABSTRACT

The invention relates to new fluorine-containing macrocyclic metal complexes that consist of a complexing agent of formula I and at least one metal ion of an element of atomic numbers 21–29, 42, 44 or 57–83

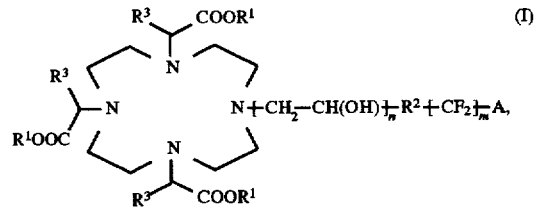

in which n, $R^1$, $R^2$, $R^3$ and A have a different meaning, agents containing these compounds, their use as NMR and x-ray diagnostic agents as well as process for the production of these compounds and agents.

15 Claims, No Drawings

FLUORINE-CONTAINING MACROCYCLIC METAL COMPLEXES

This application is a 371 of PCT/EP94/01377 dated Apr. 29, 1994.

The invention relates to the object characterized in the claims, i.e., fluorine-containing macrocyclic metal complexes, agents containing these compounds, their use as NMR diagnostic agents as well a process for the production of these compounds and agents.

With the aid of modern diagnostic methods, it is possible to depict extremely small morphological structures at a resolution that comes close to that of the tissue sections of anatomy textbooks. This enormously high resolution is achieved, on the one hand, by constantly improved hardware, but, on the other hand, also with the aid of contrast media. With the various known methods, such as ultrasonic diagnosis, diagnostic radiology, nuclear medicine and even nuclear spin tomography, however, it is not possible to obtain information on the metabolic-physiological state of a tissue in the living organism. For a more exact diagnosis and especially for planning and monitoring the course of therapeutic intervention, however, such knowledge is of considerable importance, since an optimum treatment can be successful only if a statement on its effect is possible early on.

It is known that an important factor in metabolic-physiological activity is temperature. The determination of this tissue temperature provides important information on the function and state of the cells, so that it is desirable to locate sites that have temperatures which deviate from normal body temperature. This makes it possible to identify pathologically altered tissue and optionally to perform treatment.

Body temperature is a product of the activity of energy metabolism and is subject to varied influences.

Blood flow represents a significant value of influence on local tissue temperature; via blood flow the body attempts to offset temperature drops that occur constantly [K. Brück, Heat Balance and Temperature Regulation, in: Physiologie des Menschen [Human Physiology], R. F. Schmidt, G. Thews (Editors), Springer Verlag, 23rd Edition, 1987]. The measurement of temperature therefore offers a way to delimit local increased blood circulation (e.g., in the case of inflammations) or restricted blood circulation (e.g., in ischemic regions) in a tissue against its healthy environs.

In the case of hyperthermia treatment for tumor diseases, the measurement of tissue temperature is an important parameter for monitoring the course of the radiation. At the moment, only invasive methods can be used for this purpose [P. Fessenden, Direct Temperature Measurement, in: Hyperthermia in Cancer Treatment, Cancer Research, 44 (Suppl.), 4703s–4709s, 1984].

It is now known that the chemical shift of signals in in vitro NMR spectroscopy is also a function of temperature. This influence is caused by intermolecular and intramolecular interactions. In high-resolution NMR spectroscopy, intermolecular interactions, e.g., with the solvent, quite decisively determine the chemical shift. The solvation of the molecule under study, including intermolecular aggregation and hydrogen bridging, depends greatly on temperature. Hydrogen bridge bonds are broken at elevated temperatures and thus change the chemical environment of the atomic nuclei. In the case of substances that form strong intermolecular hydrogen bridge bonds, the temperature coefficient of the chemical shift is especially large. With the aid of calibration curves, temperature can then be determined exactly from the chemical shift that is measured empirically. In this case, particularly the aliphatic alcohols, which tend toward strong hydrogen bridge bonds, have proven to be of value:

Methanol $CH_3OH$: $T=409.0-36.54\ \Delta\delta-21.85\ (\Delta\delta)^2$

Ethylene glycol $HOCH_2-CH_2OH$: $T=466.5-102.00\ \Delta\delta$ in which a $\Delta\delta$ is the difference in the chemical shifts between the OH and CH signals in ppm and T is absolute temperature in K [R. Duerst, A. Merbach, Rev. Sci. Instrum. 36, 1896 (1965)].

The change in the chemical shift with temperature due to intermolecular interaction is by no means limited to the proton; rather it is a general property of all magnetically active atomic nuclei, so that a whole series of temperature standards have been proposed in the literature.

| Standard Substance | Atomic Nuclei | Temp.-gradient ppm/K | Literature* |
|---|---|---|---|
| Methanol | proton | 0.015 | (1) |
| ethylene glycol | proton | 0.016 | (1) |
| $CH_2I_2$/cyclooctane | carbon | 0.07 | (2) |
| $CH_3I$/tetramethyl-silane | carbon | 0.02 | (2) |
| MgATP complex | phosphorus | 0.012 | (3) |
| $K_3Co(CN)_6$ | cobalt | 1.504 | (4) |
| Co-acetylacetonate | cobalt | 3.153 | (4) |
| $(CBrF_2)_2/CClF2)_2$ | fluorine | 0.0071 | (5) |
| $CFCl_3/CBr_2F_2$ | fluorine | 0.0012 | (5) |
| perfluorotributyl-amine | fluorine | 0.0003 | (6) |
| $(CH_3)_2TlNO_3$ | thallium | 0.44 | (7) |
| methanol | deuterium | 0.015 | (8) |

*For bibliographic index, see appendix

Further, a $^{13}$C-NMR thermometer has been proposed which is based on the change in the complexing constants between shifting reagent $Yb(fod)_3$ and acetone [H. J. Schneider, W. Freitag, M. Schommer, J. Magn. Reson. 18, 393 (1973)]. This process can be used only in organic solvents, however.

In virtually all organic compounds, the influence of intramolecular interactions on the chemical shift is too small to be able to use it for temperature measurements. In the literature, only one example of this type is described, in which the intramolecular rotational barrier in furfural and the associated linear changes in the $^{13}$C-NMR spectrum were used for temperature measurement [S. Combrisson, T. Prange, J. Magn. Reson. 19, 108 (1973)]. This process is suitable, however, only in a very narrow temperature range, and this measurement range depends greatly on the magnetic measuring field strength used.

Use of these methods for in vivo temperature measurement of body tissues is as yet unsuccessful, however, for various reasons. Thus, most of the compounds described in the literature cannot be mixed with water, or are soluble only in nonpolar organic solvents, such as chloroform. Thus, use in intact biological systems is virtually impossible. Although the introduction of a pure perfluorotributylamine bubble into a rabbit's eye and subsequent temperature measurement are possible [B. A. Berkowitz, J. T. Handa, C. A. Wilson, NMR in Biomedicine 5, 65 (1992)], this process is highly invasive and cannot be transferred to other organs. Some of the water-soluble compounds such as methanol, ethylene glycol, $K_3Co(CN)_6$ and thallium salts must be excluded from the start because of their high toxicity. Of the substances described, theoretically only the MgATP complex is suitable as an endogenous temperature sensor. Since the relative MgATP concentration in cytosol is small (around 10 mmol/kg) and cannot be increased by external administration because of the creatinine-kinase equilibrium and since in addition the phosphorus nuclei are insensitive and the chemical shift is also heavily dependent on the ionic strength and the pH of the medium, a precise temperature determination with $^{31}$P-NMR measurements of MgATP within a reasonable time is not possible. Thus, all temperature sensors that are described in the literature are unsuitable for an intracellular in vivo temperature measurement in routine clinical diagnosis.

The object of this invention was therefore to find suitable compounds for in vivo temperature measurement by means of NMR spectroscopy.

These compounds must meet the following requirements:

a) They must react to a change of temperature with a changed resonance frequency in the NMR spectrum, b) They must exhibit a pronounced chemical shift per degree of temperature change, c) They must exhibit pharmacokinetics that is suitable for diagnostic applications, d) They must exhibit a concentration in the target tissues that is high enough for measuring, e) They must exhibit good compatibility and low toxicity, f) They must exhibit metabolic stability, g) They must exhibit high chemical stability and long shelf life and h) They must exhibit good water-solubility.

The fluorine-containing macrocyclic metal complexes according to the invention and the solutions that are prepared from them meet the above-mentioned requirements in a surprising way. Moreover, they are not only very well suited as temperature sensors for measuring tissue temperature, but in the same way are also suited as contrast media in the case of imaging NMR processes as well as in diagnostic radiology.

For use of the complex compounds according to the invention as temperature sensors in NMR diagnosis, preferably metal complexes with paramagnetic metal ions of the elements of atomic numbers 21–29, 42, 44, 58–70 are suitable.

In addition to the required large temperature gradients (point b), the compounds according to the invention are also especially distinguished by very good compatibility (point e).

The fluorine-containing macrocyclic metal complexes according to the invention consist of at least one metal ion of an element of atomic numbers 21–29, 42, 44 or 57–83 and a complexing agent of general formula I

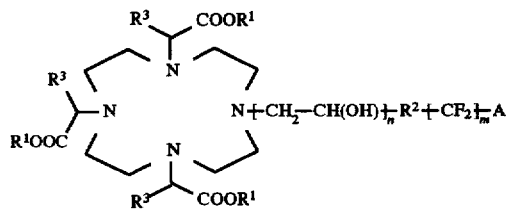

in which n and m, independently of one another, stand for the numbers 0 or 1, $R^1$ independently of one another, stand for a hydrogen atom or a metal ion equivalent, $R^3$ stands for a hydrogen atom, a straight-chain or branched $C_1$–$C_{10}$ alkyl group, which is optionally substituted by 1–5 $C_1$–$C_6$ alkoxy groups, hydroxy-$C_1$–$C_6$ alkyl groups and/or hydroxy groups, $R^2$ stands for a straight-chain or branched $C_1$–$C_{10}$ alkylene group that is substituted by 1 to 3 —$CF_3$ groups and which optionally is interrupted by 1 to 5 oxygen atoms and/or carbonyl groups and/or optionally is substituted by 1 to 5 hydroxy groups, $C_1$–$C_6$ alkoxy-$C_1$–$C_6$ alkyl groups, $OR^4$, —CO—$NR^5R^6$, —$NR^5R^6$ and/or —$NR^5$—CO—$R^6$ radicals, in which $R^4$ stands for a straight-chain or branched $C_1$–$C_4$ alkyl radical and $R^5$, $R^6$, independently of one another, have the meaning of $R^3$, and A if m means the number 1, stands for a fluorine atom, and, if m means the number 0, A stands for a hydrogen atom or a second macrocyclic radical of general formula II,

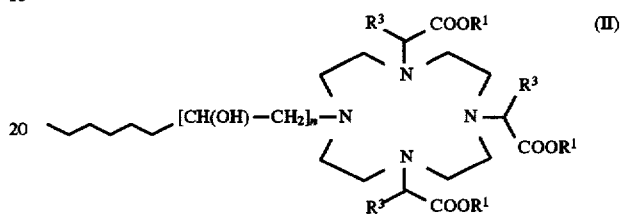

in which n, $R^1$ and $R^3$ have the indicated meanings, as well as their salts with inorganic and/or organic bases or amino acids and/or their $C_1$–$C_6$ alkyl or $C_6$–$C_{10}$ aryl or aralkyl esters or amides, and at least two radicals $R^1$ stand for a metal ion equivalent.

Preferred are compounds in which the radical

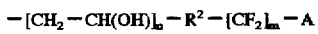

stands for a —$CH_2$—CH(OH)—$CF_3$, —$CH_2$—C(OH) $CF_3$—$CH_3$—, —$CH_2$—CH(OH)—$C(CF_3)_3$ or —$CH_2$—CH (OH)—$CH_2O$—$C(CF_3)_3$ group.

Surprisingly enough, the changes in the chemical shifts are essentially intramolecular in origin and thus are independent of outside influences, such as ionic strength, pH, and oxygen partial pressure, i.e., the dependence of the chemical shift on temperature is based only on the interaction between a central ion and the atomic nuclei present in the ligand.

It is further surprising that this chemical shift, which is caused by intramolecular interaction, can be used for in vivo temperature measurement.

The temperature gradients depend on the measured atomic nuclei, the chemical structure of the ligand, and the central ion.

In this case, depending the complex and central ion, positive and negative temperature gradients can be observed, i.e., the temperature effect on the chemical shift of the signals caused by the complexes can move in different directions. Thus, the possibility arises of considerably increasing the precision of the temperature measurement by mixing the two complexes with different signs in the temperature gradients.

A quite critical advantage of this family of compounds for localized in vivo NMR spectroscopy lies in the fact that the signals that are exclusively for temperature determination, which are caused by the fluorine nuclei, are used. Since these signals, in a completely different spectral range, can be observed as signals which are caused by endogenous substances (i.e., essentially by the protons of tissue water), the use of the substances according to the invention allows the almost distortion-free measurement of temperature-sensitive signals.

The great flexibility of the chemical structure of the ligand, which can be adapted to the measuring problem to be solved, offers another advantage. By appropriately adjusting longitudinal relaxation time $T^1$ of the measurement signal, e.g., optimum sensitivity can be achieved. For localized spectroscopic methods, which are based on a spin echo formation, transversal relaxation time $T_2$ can be adjusted optimally in the same way.

In the same way, the metal complexes according to the invention are also suitable as contrast media in imaging NMR processes or in diagnostic radiology, and in the case of imaging NMR processes, complexes with metal ions of the elements of atomic numbers 21–29, 42, 44 or 57–70 are preferably used, and in diagnostic radiology, complexes with metal ions of the elements of atomic numbers 21–29, 42, 44 or 57–83 are preferably used.

The production of the fluorine-containing complexing agents of general formula I according to the invention (i.e., of compounds in which $R^1$ stands for a hydrogen atom) is done by 1,4,7-tris-(carboxymethyl)-1,4,7,10-tetraazacyclododecane being alkylated with epoxides or halogen compounds.

Compounds of formula I, in which $R^3$ does not equate to hydrogen, can be produced analogously to the process described in DE 41 40 779, by side chain —$R^2$—$(CF_2)_m$—A being first introduced by reacting the corresponding epoxide with tricyclotridecane. After cleavage of the formyl group of the intermediate product produced, the product thus obtained is reacted with a compound of general formula III,

(III)

in which X stands for a nucleofuge, e.g., for a halogen or a sulfonic acid radical and $R^7$ stands for a hydrogen atom or for an acid protective group, preferably for a butyl group.

Instead of the tricyclotridecane used above, tris (benzyloxycarbonyl)cyclene can also be alkylated with epoxides (see J. Chem. Soc. Perkin Trans. I, 12, 3329 [1991]).

The epoxides that are required for reactions are commercially available (3,3,3-trifluoro-2,3-epoxy-propane, Fluorochem Ltd. Derbyshire, U.K.), known in the literature (2-trifluoromethyl-2,3-epoxy-propane, McBee et al., J. Amer. Chem. Soc. 78, (1956), 4053, 4055, R. H. Groth, J. Org. Chem. 25, (1960), 102, 103) and can be easily obtained or produced from commercially available precursors according to the processes that are well-known to one skilled in the art.

Thus, nonafluoro-t-butyl-2,3-epoxypropyl ether can be obtained from perfluoro-t-butanol (Fluorochem Ltd. Derbyshire, U.K.) and epichlorohydrin can be obtained according to the process for glycide ether synthesis (V. Ulbrich and H. Rejková, Collect. 24 (1959), 2114; Houben-Weyl, Methoden der Organischen Chemie [Methods of Organic Chemistry], Volume VI/3, p. 421 ff, (1965) Georg Thieme Verlag, Stuttgart).

The 4,4,4-trifluoromethyl-3,3-bis(trifluoromethyl)-2,3-epoxypropane is produced from octafluorocyclobutane (Fluorochem Ltd., Derbyshire, U.K.) by perfluoroisobutylene (Syntheses of Fluororganic Compounds, edited by I. L. Knunyants and G. G. Yakoleson, Springer-Verlag Berlin, Heidelberg, New York, Tokyo, p. 9 (1985)) and 4,4,4-trifluoro-3,3-bis(trifluoromethyl)-but-1-ene (ibid. p. 11).

The olefin is converted to the epoxide by peracids such as 3-chloroperbenzoic acid (Kaufware Fa. [Commercial Products Company] Aldrich, Steinheim, Germany, F. Fringueli et al., Tetrahedron Letters 30, 1427 (1989)), 4-nitrobenzoic acid (D. Swern et al., Chem. and Ind. 1304, (1962)), trifluoroperacetic acid (W. D. Emmons and A. S. Pogano, Am. Soc. 77, 89, (1955)) or peroxyiminoacetic acid produced in situ (Y. Ogata and Y. Sawoki, Tetrahedron 20, 2064, (1964)).

For the conversion of an olefin to an epoxide, the addition of hypohalide to halohydrin (Houben-Weyl, Methoden der Organischen Chemie, Volume V/3, p. 762 ff, (1962) Georg Thieme Verlag, Stuttgart), followed by cyclization (Houben-Weyl, Methoden der Organischen Chemie, Volume VI/3, p. 374 ff, (1965) to oxiran, is also suitable.

The reaction of 1,4,7-triscarboxymethyl-1,4,7,10-tetraazacyclododecane with epoxides is done in solvents at temperatures of between 10° and 150° C., preferably at 50°–80° C. As solvents, all inert solvents are suitable. The reaction is done with the addition of bases. The bases can be added in solid or dissolved form. The bases that can be considered include lithium hydroxide, sodium hydroxide, potassium hydroxide, alkali- and alkaline-earth carbonates, and -oxides, or organic bases, such as tertiary amines, e.g., triethylamine or diisopropylethylamine, N-methylmorpholine or tetramethylpiperidine.

The reaction of 1,4,7-triscarboxymethyl-1,4,7,10-tetraazacyclododecane with halogen compounds can also be done in solid or liquid form. Preferred solvents are dioxane, tetrahydrofuran, dimethylformamide, dimethylacetamide and methanol, ethanol, propanol, isopropanol and water. The reaction is done with the addition of bases (as indicated above) at temperatures of between 40° C. and 150° C., preferably at 75° to 110° C.

The production of the metal complexes according to the invention from these complexing agents is done in the way that was disclosed in German laid-open specification 34 01 052 and EP 0 450 742 and EP 0 413 405, by dissolving or suspending the metal oxide or a metal salt (for example, nitrate, acetate, carbonate, chloride or sulfate) of the element of atomic numbers 21–29, 42, 44, 57–83 in water and/or a lower alcohol (such as methanol, ethanol or isopropanol) and reacting the equivalent amount of complexing ligand with the solution or suspension, and then, if desired, substituting present acid hydrogen atoms by cations of inorganic and/or organic bases or amino acids or reacting them to esters or amides.

The neutralization of free acid groups that are optionally still present is done with the aid of inorganic bases (for example, hydroxides, carbonates or bicarbonates) of, for example, sodium, potassium, lithium, magnesium or calcium and/or organic bases, such as, i.a., primary, secondary and tertiary amines, such as, for example, ethanolamine, morpholine, glucamine, N-methylglucamine and N,N-dimethylglucamine, as well as basic amino acids, such as, for example, lysine, arginine and ornithine or amides of initially neutral and acidic amino acids. As an alternative, free acid groups can be converted completely or partially to ester or amide groups in a way known in the art.

For the production of neutral complex compounds, for example, enough of the desired bases can be added to the acid complex salts in aqueous solution or suspension to ensure that the neutral point is reached. The solution obtained can then be evaporated to dryness in a vacuum. Often, it is advantageous to precipitate the neutral salts that are formed by adding water-miscible solvents, such as, for example, lower alcohols (methanol, ethanol, isopropanol and others), lower ketones (acetone and others), or polar ethers (tetrahydrofuran, dioxane, 1,2-dimethoxyethane and others) and thus to obtain crystallizates that are easily isolated and readily purified. It has proven especially advantageous to add the desired base as early as during complexing of the reaction mixture and as a result to eliminate a process step.

If the acid complex compounds contain several free acid groups, it is often advisable to produce neutral mixed salts that contain both inorganic and organic cations as counterions.

The pharmaceutical agents according to the invention are preferably produced in a concentration of 1 μmol-1 mol/l. They are generally dosed in amounts of 0.005–20 mmol/kg of body weight, preferably 0.05–5 mmol/kg of body weight. They are intended for enteral and parenteral administration. The agents according to the invention meet the varied requirements for suitability as diagnostic agents for NMR tomography and NMR spectroscopy. Further, they possess the high effectiveness that is necessary to burden the body with the smallest possible amounts of foreign substances and the good compatibility that is necessary to preserve the noninvasive nature of the studies.

The good water solubility of the complexes and low osmolality of the agents according to the invention make it possible to produce highly concentrated solutions, so that the volume burden on the circulatory system is kept within reasonable limits and the dilution is compensated for by the bodily fluid. Thus, the complexes and agents according to the invention are very well suited not only as temperature sensors in NMR spectroscopy but also as contrast media in imaging NMR methods as well as in diagnostic radiology.

Further, the agents according to the invention exhibit not only high stability in vitro, but also surprisingly high stability in vivo, so that any release or exchange of the ions that are bound in the complexes occurs only extremely slowly within the time that it takes for the new contrast media to be completely excreted again.

By using the very well-tolerated complexes as new measuring sensors, it has thus been possible to perform site-resolved spectroscopy in smaller volumes (e.g., 10 cm$^3$) and to determine temperature precisely in shorter measurement times without disruption or superposition by other molecules. The above-mentioned compounds are also suitable for in vivo imaging (NMR imaging).

The following examples are used to explain the object of the invention, without intending that they be limited to this object.

EXAMPLE 1 a) 10-(2-Hydroxy-2-trifluoromethyl-ethyl)-1,4,7-tris-carboxymethyl-1,4,7,10-tetraazacyclododecane 12.94 g (115.44 mmol) of (1,1,1-trifluoro-2,3-epoxypropane) and 10 g (28.86 mmol) of 1,4,7-triscarboxymethyl-1,4,7,10-tetraazacyclododecane are dissolved in a mixture of 50 ml of dioxane/80 ml of water, and the pH is brought to 10 with 6N potassium hydroxide solution. It is stirred for 24 hours at 70° C. with exclusion of pressure. It is evaporated to dryness, the residue is taken up with 300 ml of water/50 ml of methanol and extracted twice with 100 ml of tert-butyl methyl ether. The aqueous solution is adjusted to pH 1 with 5N hydrochloric acid and evaporated to dryness. The residue is boiled out (extracted) with 200 ml of methanol/80 ml of methylene chloride. It is cooled in an ice bath and precipitated potassium chloride is filtered out. The filtrate is concentrated by evaporation in a vacuum, the residue is dissolved in 45 ml of water/20 ml of ethanol and then put on a column of poly-(4-vinylpyridine). The product is eluted with a solution of ethanol/water 1:3. After concentration by evaporation in a vacuum, the residue is chromatographed on a reversed-phase column (RP 18/mobile solvent=gradient of water/tetrahydrofuran). After concentration by evaporation of the main fraction, 10.81 g (68% of theory) of a strongly hygroscopic, vitreous solid is obtained.

Water content: 11.3% Analysis (relative to anhydrous substance): Cld: C 44.54 H 6.38 N 12.22 F 12.43 Fnd: C 44.31 H 6.51 N 12.12 F 12.19 b) Lanthanum complex of 10-(2-hydroxy-2-trifluoromethyl-ethyl)-1,4,7-tris-carboxymethyl-1,4,7,10-tetraazacyclododecane 4.69 g (10.24 mmol) of the title compound of Example 1a is dissolved in 50 ml of water and 1.67 g (5.12 mmol) of lanthanum oxide is added. It is stirred for 3 hours at 90° C. The solution is stirred for one hour with 2 ml of acidic ion exchanger (ANB 252c/H$^+$ form) and 2 ml of weakly basic exchanger IRA 67/OH$^-$ form) at room temperature. Exchanger is filtered out, and the filtrate is freeze-dried.

Yield: 6.53 g (94% of theory) of a vitreous solid Water content: 8.0% Analysis (relative to anhydrous substance): Cld: C 34.36 H 4.41 N 9.43 F 9.59 La 23.37 Fnd: C 34.21 H 4.50 N 9.33 F 9.40 La 22.09 c) Praseodymium complex of 10-(2-hydroxy-2-trifluoromethyl-ethyl)-1,4,7-tris-carboxymethyl-1,4,7,10-tetraazacyclododecane 5.28 g (11.51 mmol) of the title compound of Example 1a is dissolved in 50 ml of water and 3.66 g (11.51 mmol) of praseodymium(III) acetate is added. It is heated for 2 hours to 90°C. and then evaporated to dryness in a vacuum. The residue is taken up in 50 ml of water and again evaporated to dryness. The residue is dissolved in 100 ml of water and stirred for 1 hour with 2 ml of acidic ion exchanger (AMB 252c/H$^+$ form) and 5 ml of weakly basic exchanger (IRA 67/OH$^-$ form). Exchanger is filtered out, and the filtrate is freeze-dried.

Yield: 95% of theory of a light greenish powder Analysis: Cld: C 34.24 H 4.39 N 9.40 F 9.56 Pr 23.63 Fnd: C 34.51 H 4.20 N 9.62 F 9.80 Pr 23.40 d) Dysprosium complex of 10-(2-hydroxy-2-trifluoromethyl-ethyl)-1,4,7-tris-carboxymethyl-1,4,7,10-tetraazacyclododecane Analogously to 1b, dysprosium oxide instead of lanthanum oxide was used.

Yield: 95% of theory of a colorless amorphous powder Water content: 7.5% Analysis (relative to anhydrous substance): Cld: C 33.05 H 4.24 N 9.07 F 9.23 Dy 26.23 Fnd: C 33.15 H 4.36 N 8.80 F 9.01 Dy 26.10 e) Europium complex of 10-(2-hydroxy-2-trifluoromethyl-ethyl)-1,4,7-tris-carboxymethyl-1,4,7,10-tetraazacyclododecane Analogously to Example 1b, europium oxide instead of lanthanum oxide was used.

Yield: 94% of theory of a colorless powder Water content: 7.1% Analysis (relative to anhydrous substance): Cld: C 33.62 H 4.31 N 9.22 F 9.38 Eu 25.02 Fnd: C 33.30 H 4.58 N 9.33 F 9.09 Eu 24.88

EXAMPLE 2 a) 10-(2-Hydroxy-2-trifluoromethyl-propyl)-1,4,7-tris-carboxymethyl-1,4,7,10-tetraazacyclododecane 10.29 g (86.58 mmol) of 2,3-epoxy-2-trifluoromethylpropane and 10 g (28.86 mmol) of 1,4,7-triscarboxymethyl-1,4,7,10-tetraazacyclododecane are dissolved in a mixture of 50 ml of dioxane/80 ml of water, and the pH is brought to 10 with 6N potassium hydroxide solution. It is stirred for 24 hours at 70° C. (with exclusion of pressure). It is evaporated to dryness, the residue is taken up with 300 ml of water/50 ml of methanol and extracted twice with 100 ml of tert-butyl methyl ether. The aqueous solution is adjusted to pH 1 with 5N hydrochloric acid and evaporated to dryness. The residue is boiled out (extracted) with 200 ml of methanol/80 ml of methylene chloride. It is cooled in an ice bath and precipitated potassium chloride is filtered out. The filtrate is concentrated by evaporation in a vacuum, the residue is dissolved in 45 ml of water/20 ml of ethanol and then put on a column of poly-(4-vinylpyridine). The product is eluted with a solution of ethanol/water 1:3. After concentration by evaporation in a vacuum, the residue is chromatographed on a reversed-phase column (RP 18/mobile solvent=gradient of water/tetrahydrofuran). After concentration by evaporation of the main fraction, 11.04 g (71% of theory) of a strongly hygroscopic, vitreous solid is obtained.

Water content: 9.3% Analysis (relative to anhydrous substance): Cld: C 45.76 H 6.01 N 18.86 F 12.06 Fnd: C 45.81 H 6.29 N 18.99 F 11.87 b) Dysprosium complex of 10-(2-hydroxy-2-trifluoromethyl-propyl)-1,4,7-tris-carboxymethyl-1,4,7,10-tetraazacyclododecane 5 g (10.24 mmol) of the title compound of Example 2a is dissolved in 50 ml of water and 1.91 g (5.12 mmol) of samarium oxide is added. It is stirred for 3 hours at 90° C. The solution is stirred for one hour with 2 ml of acidic ion exchanger (ANB 252 c/H$^+$ form) and 2 ml of weakly basic exchanger IRA 67/OH$^-$ form) at room temperature. Exchanger is filtered out, and the filtrate is freeze-dried.

Yield: 6.70 g (96% of theory) of a vitreous solid Water content: 7.3% Analysis (relative to anhydrous substance): Cld: C 34.21 H 4.47 N 8.87 F 9.02 Dy 25.71 Fnd: C 34.10 H 4.59 N 8.63 F 8.82 Dy 25.50 c) Europium complex of 10-(2-hydroxy-2-trifluoromethyl-propyl)-1,4,7-tris-(carboxymethyl)-1,4,7,10-tetraazacyclododecane Analogously to Example 2b, europium oxide instead of dysprosium oxide was used.

Yield: 96% of theory of a colorless amorphous powder Water content: 8.1% Analysis (relative to anhydrous substance): Cld: C 34.79 H 4.54 N 9.02 F 9.17 Eu 24.45 Fnd: C 34.59 H 4.67 N 8.87 F 9.05 Eu 24.23 d) Praseodymium complex of 10-(2-hydroxy-2-trifluoromethyl-propyl)-1,4,7-tris-(carboxymethyl)-1,4,7,10-tetraazacyclododecane 5.44 g (11.51 mmol) of the title compound of Example 2a is dissolved in 50 ml of water and 3.66 g (11.51 mmol) of praseodymium(III) acetate is added. It is heated for 2 hours to 90° C. and then evaporated to dryness in a vacuum. The residue is taken up in 50 ml of water and again evaporated to dryness. The residue is dissolved in 100 ml of water and stirred for 1 hour with 2 ml of acidic ion exchanger (AMB 252c/H$^+$ form) and 5 ml of weakly basic exchanger (IRA 67/OH$^-$ form). Exchanger is filtered out, and the filtrate is freeze-dried.

Yield: 92% of theory of a greenish-colored powder Water content: 7.3% Analysis (relative to anhydrous substance): Cld: 35.42 H 4.62 N 9.18 F 9.34 Pr 23.09 Fnd: 35.21 H 4.78 N 9.03 F 9.15 Pr 22.88

EXAMPLE 3 a) t-(Nonafluoro)-butyl-2,3-epoxypropyl ether

In 100 ml of absolute ether, 24.78 g (105 mmol) of nonafluoro-t-butanol is dissolved and mixed in portions with 2.30 g (100 mmol) of sodium. After all sodium is dissolved, it is mixed in portions with 9.25 g (100 mmol) of epichlorohydrin and stirred first for 1 hour at room temperature, then for 2 hours at reflux temperature. The ether is distilled on a column, and the residue is heated for 1 hour to 60° C. After cooling, solid is suctioned off, and the filtrate is distilled with slight vacuum (30 mbar, 140° C. bath) in a bulb tube.

Yield: 23.35 g (21.4% of theory) of content after GC: 98.2% Analysis (relative to anhydrous substance): Cld: C 28.78 H 1.73 F 58.54 Fnd: C 28.62 H 1.78 F 58.63 b) 10-(2-Hydroxy-3-(tert-nonafluoro-butoxy-propyl)-1,4,7-tris-carboxymethyl-1,4,7,10-tetraazacyclododecane 25.29 g (86.58 mmol) of the title compound of Example 3a and 10 g (28.86 mmol) of 1,4,7-triscarboxymethyl-1,4,7,10-tetraazacyclododecane are dissolved in a mixture of 50 ml of dioxane/80 ml of water, and the pH is brought to 10 with 6N potassium hydroxide solution. It is stirred for 24 hours at 70° C. (with exclusion of pressure). It is evaporated to dryness, the residue is taken up with 300 ml of water/50 ml of methanol, and it is extracted twice with 100 ml of tert-butyl methyl ether. The aqueous solution is adjusted to pH 1 with 5N hydrochloric acid and evaporated to dryness. The residue is boiled out (extracted) with 200 ml of methanol/80 ml of methylene chloride. It is cooled in an ice bath, and potassium chloride is filtered out. The filtrate is concentrated by evaporation in a vacuum, the residue is dissolved in 45 ml of water/20 ml of ethanol and then put on a column of poly-(4-vinylpyridine). The product is eluted with a solution of ethanol/water 1:3. After concentration by evaporation in a vacuum, the residue is chromatographed on a reversed-phase column (RP 18/mobile solvent=gradient of water/tetrahydrofuran). After concentration by evaporation of the main fraction, 10.55 g (63% of theory) of a strongly hygroscopic, vitreous solid is obtained.

Water content: 9.1% Analysis (relative to anhydrous substance): Cld: C 39.50 H 4.89 N 8.77 F 26.78 Fnd: C 39.31 H 4.99 N 8.51 F 26.57 c) Dysprosium complex of 10-(2-hydroxy-3-(tert-nonafluoro-butoxy)-propyl)-1,4,7-tris-(carboxymethyl)-1,4,7,10-tetraazacyclododecane 5 g (7.83 mmol) of the title compound of Example 3b is dissolved in 50 ml of water, and 1.46 g (3.91 mmol) of dysprosium oxide is added. It is stirred for 3 hours at 90° C. The solution is stirred for one hour with 2 ml of acidic ion exchanger (AMB 252c/H$^+$ form) and 2 ml of weakly basic exchanger (IRA 67/OH$^-$ form) at room temperature. Exchanger is filtered out, and the filtrate is freeze-dried.

Yield: 6.25 g (93% of theory) of a vitreous solid Water content: 7.0% Analysis (relative to anhydrous substance): Cld: C 31.61 H 3.54 N 7.02 F 21.43 Dy 20.36 Fnd: C 31.42 H 3.71 N 6.90 F 21.20 Dy 20.18 d) Europium complex of 10-(2-hydroxy-3-(tert-nonafluorobutoxy)-propyl)-1,4,7-tris-(carboxymethyl)-1,4,7,10-tetraazacyclododecane Analogously to Example 3c, europium oxide instead of dysprosium oxide was used.

Yield: 97% of theory of a colorless amorphous powder Water content: 6.9% Analysis (relative to anhydrous substance): Cld: C 32.03 H 3.58 N 7.12 F 21.71 Eu 19.30 Fnd: C 31.88 H 3.70 N 7.01 F 21.50 Eu 19.09 e) Praseodymium complex of 10-(2-hydroxy-3-(tert-nonafluorobutoxy)-propyl)-1,4,7-tris-(carboxymethyl)-1,4,7,10-tetraazacyclododecane 7.35 g (11.51 mmol) of the title compound of Example 3b is dissolved in 50 ml of water and 3.66 g (11.51 mmol) of praseodymium(III) acetate is added. It is heated for 2 hours to 90° C. and then evaporated to dryness in a vacuum. The residue is taken up in 50 ml of water and again evaporated to dryness. The residue is dissolved in 100 ml of water and stirred for 1 hour with 2 ml of acidic ion exchanger (AMB 252c/H⁺ form) and 5 ml of weakly basic exchanger (IRA 67/OH⁻ form). Exchanger is filtered out, and the filtrate is freeze-dried.

Yield: 94% of theory of a green solid Water content: 3.5% Analysis (relative to anhydrous substance): Cld: C 32.49 H 3.64 N 7.22 F 22.02 Pr 18.15 Fnd: C 32.28 H 3.78 N 7.05 F 21.88 Pr 17.92

EXAMPLE 4 a) 4,4,4-Trifluoro-3,3-bis(trifluoromethyl)-1,2-epoxybutane 32.9 g (105 mmol) of 3-chloroperbenzoic acid with a peracid content of 55% is added in portions with stirring and cooling with water to a solution of 24.6 g (100 mmol) of 4,4,4-trifluoro-3,3-bis(trifluoromethyl)-but-1-ene in 150 ml of absolute diethyl ether. After addition is completed, it is refluxed for 3 hours. It is allowed to cool, and the solution is stirred in cold, saturated sodium bicarbonate solution. The ethereal solution is separated, washed with sodium chloride solution, dried on sodium sulfate and concentrated by evaporation on a column. The residue is purified by bulb tube distillation (vacuum 30 mbar, 130° C. bath).

Yield: 18.95 g (73.3% of theory) of content after GC: 98.7% Analysis (relative to anhydrous substance): Cld: C 27.50 H 1.15 F 65.24 Fnd: C 27.63 H 1.22 F 65.12 b) 10-(2-Hydroxy-3,3,3-tris(trifluoromethyl)-propyl)-1,4,7-tris-carboxymethyl-1,4,7,10-tetraazacyclododecane 22.69 g (86.58 mmol) of the title compound of Example 4a and 10 g (28.86 mmol) of 1,4,7-triscarboxymethyl-1,4,7,10-tetraazacyclododecane are dissolved in a mixture of 50 ml of dioxane/80 ml of water, and the pH is brought to 10 with 6N potassium hydroxide solution. It is stirred for 24 hours at 70° with exclusion of pressure. It is evaporated to dryness, the residue is taken up with 300 ml of water/50 ml of methanol, and it is extracted twice with 100 ml of tert-butyl methyl ether. The aqueous solution is adjusted to pH 1 with 5N hydrochloric acid and evaporated to dryness. The residue is boiled out (extracted) with 200 ml of methanol/80 ml of methylene chloride. It is cooled in an ice bath, and potassium chloride is filtered out. The filtrate is concentrated by evaporation in a vacuum, the residue is dissolved in 45 ml of water/20 ml of ethanol and then put on a column of poly-(4-vinylpyridine). The product is eluted with a solution of ethanol/water 1:3. After concentration by evaporation in a vacuum, the residue is chromatographed on a reversed-phase column (RP 18/mobile solvent=gradient of water/tetrahydrofuran). After concentration by evaporation of the main fraction, 13.87 g (71% of theory) of a strongly hygroscopic, vitreous solid is obtained.

Water content: 10.1% Analysis (relative to anhydrous substance): Cld: C 39.48 H 4.80 N 9.21 F 28.10 Fnd: C 39.29 H 4.95 N 9.05 F 28.03 c) Dysprosium complex of 10-(2-hydroxy-3,3,3-tris (fluoromethyl)-propyl)-1,4,7-tris-(carboxymethyl)-1,4,7,10-tetraazacyclododecane 5 g (8.22 mmol) of the title compound of Example 4b) is dissolved in 50 ml of water and 1.53 g (4.11 mmol) of dysprosium oxide is added. It is stirred for 3 hours at 90° C. The solution is stirred for one hour with 2 ml of acidic ion exchanger (AMB 252c/H⁺ form) and 2 ml of weakly basic exchanger (IRA 67/OH⁻ form) at room temperature. Exchanger is filtered out, and the filtrate is freeze-dried.

Yield: 6.43 g (95% of theory) of a vitreous solid Water content: 6.7% Analysis (relative to anhydrous substance): Cld: C 31.28 H 3.41 N 7.30 F 22.27 Dy 21.16 Fnd: C 31.04 H 3.51 N 7.14 F 22.11 Dy 21.04 d) Europium complex of 10-(2-hydroxy-3,3,3-tris (trifluoromethyl)-propyl)-1,4,7-tris(carboxymethyl)-1,4,7,10-tetraazacyclododecane Analogously to Example 4c, europium oxide instead of dysprosium oxide was used.

Yield: 97% of theory of a colorless amorphous powder Water content: 7.2% Analysis (relative to anhydrous substance): Cld: C 31.72 H 3.46 N 7.40 F 22.58 Eu 20.06 Fnd: C 31.51 H 3.59 N 7.21 F 22.35 Eu 19.87 e) Praseodymium complex of 10-(2-hydroxy-3,3,3-tris (trifluoromethyl)-propyl)-1,4,7-tris(carboxymethyl)-1,4,7,10-tetraazacyclododecane 7.00 g (11.51 mmol) of the title compound of Example 4b is dissolved in 50 ml of water and 3.66 g (11.51 mmol) of praseodymium(III) acetate is added. It is heated for 2 hours to 90° C. and then evaporated to dryness in a vacuum. The residue is taken up in 50 ml of water and again evaporated to dryness. The residue is dissolved in 100 ml of water and stirred for 1 hour with 2 ml of acidic ion exchanger (AMB 252c/H⁺ form) and 5 ml of weakly basic exchanger (IRA 67/OH⁻ form). Exchanger is filtered out, and the filtrate is freeze-dried.

Yield: 94% of theory of a light green powder Water content: 9.5% Analysis (relative to anhydrous substance): Cld: C 32.19 H 3.51 N 7.51 F 22.91 Pr 18.88 Fnd: C 32.03 H 3.63 N 7.38 F 22.70 Pr 18.64

EXAMPLE 5

The parameters that are listed in Table 1 were determined for the praseodymium complex or for the dysprosium complex of 10-(2-hydroxy-2-trifluoromethyl-ethyl)-1,4,7-triscarboxymethyl-1,4,7,10-tetraazacyclododecane (produced according to Example 1c or 1d).

TABLE 1

|  | Example No. | |
| --- | --- | --- |
|  | 1c | 1d |
| Metal atom | Praseodymium | Dysprosium |
| Temp. gradient [ppm/K] | 0.016 | 0.49 |
| Chemical shift δ [ppm] | −82.6 | −160 |
| Line width $\Delta v_{1/2}$ [Hz] | 35 | 300 |
| Relative accuracy | $0.45 \cdot 10^{-3}$ | $1.4 \cdot 10^{-3}$ |

The measurements were made on a Bruker device AC 250 in the temperature range between 26° C. and 46° C. on a 0.01 molar aqueous solution of the respective complex. The chemical shifts relate to $CFCl_3$ as an external standard.

BIBLIOGRAPHY (1) R. Duerst et al., Rev. Sci. Instrum. 36 (1965) 1896, F. Conti, Rev. Sci. Instrum. 38 (1967) 128, A. L. Van Geet, Anal. Chem. 40 (1968) 2227, A. L. Van Geet, Anal. Chem. 42 (1970) 678, C. Ammann et al., J. Magn. Reson. 46 (1982) 319;

(2) D. R. Vidrin et al., Anal. Chem. 48 (1976) 1301;

(3) R. K. Gupta et al., J. Magn. Reson. 40 (1980) 587;

(4) J. T. Bailey et al., J. Magn. Reson. 37 (1980) 353;

(5) P. E. Peterson, Anal. Chem. 50 (1978) 298;

(6) B. A. Berkowitz et al., NMR in Biomedicine 5 (1992) 65;

(7) M. J. Foster et al., J. Magn. Reson. 65 (1985) 497;

(8) K. Roth, Magn. Reson. Chem. 25 (1987) 429.

We claim:

1. A fluorine-containing macrocyclic metal complex having at least one metal ion of an element of atomic numbers 21–29, 42, 44 or 57–83 and a complexing agent of formula

I

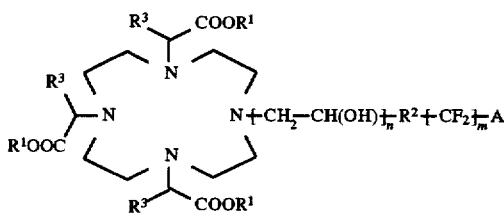

in which:
- n and m independently of one another, stand for the numbers 0 or 1;
- $R^1$ independently of one another, stand for a hydrogen atom or a metal ion equivalent;
- $R^3$ stands for a hydrogen atom, a straight-chain or branched $C_1$–$C_{10}$ alkyl group, which optionally is substituted by 1–5 $C_1$–$C_6$ alkoxy groups, hydroxy-$C_1$–$C_6$ alkyl groups and/or hydroxy groups;
- $R^2$ stands for a straight-chain or branched $C_1$–$C_{10}$ alkylene group which is substituted by 1 to 3 —$CF_3$ groups and which optionally is interrupted by 1 to 5 oxygen atoms and/or carbonyl groups and/or optionally is substituted by 1 to 5 hydroxy groups, $C_1$–$C_6$ alkoxy-$C_1$–$C_6$ alkyl groups, —$OR^4$, —CO—$NR^5R^6$, $NR^5R^6$ and/or —$NR^5$—CO—$R^6$ radicals,
  in which $R^4$ stands for a straight-chain or branched $C_1$–$C_4$ alkyl radical and $R^5$, $R^6$, independently of one another, have the meaning of $R^3$; and
- A stands for a fluorine atom when m is 1 or A stands for a hydrogen atom or a second macrocyclic radical of formula II,

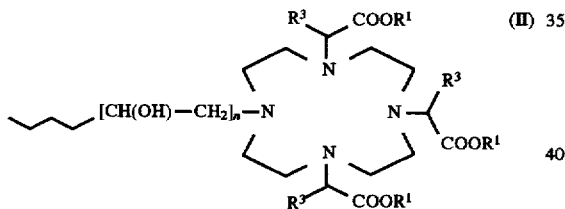

in which:
- n, $R^1$ and $R^3$ have the indicated meanings, when m is 0; and
- salts thereof with inorganic and/or organic bases or amino acids; and $C_1$–$C_6$ alkyl or $C_6$–$C_{10}$ aryl or aralkyl esters or amides thereof; provided that at least two radicals $R^1$ stand for a metal ion equivalent.

2. A fluorine-containing macrocyclic metal complex according to claim 1 wherein the radical

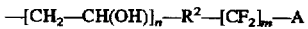

is a —$CH_2$—CH(OH)—$CF_3$, —$CH_2$—C(OH)$CF_3$—$CH_3$, —$CH_2$—CH(OH)—C($CF_3$)$_3$ or —$CH_2$—CH(OH)—$CH_2$O—C($CF_3$)$_3$ group.

3. A method for diagnostic radiology comprising conducting a diagnoses with a fluorine-containing, macrocyclic metal complex according to claim 1 as a contrast agent.

4. A method for NMR diagnosis comprising conducting a diagnosis with a fluorine-containing, macrocyclic metal complex according to claim 1 as a contrast agent.

5. A method for determining the temperature of a tissue which comprises conducting NMR spectroscopy with a fluorine-containing, macrocyclic metal complex according to claim 1 as a temperature sensor.

6. A composition for tissue temperature determination by NMR spectroscopy which comprises a fluorine-containing, macrocyclic metal complex according to claim 1.

7. The method of claim 3, where the fluorine-containing, macrocyclic metal complex is provided in a dose of 0.005–20 mmol/kg of body weight.

8. The method of claim 4, where the fluorine-containing, macrocyclic metal complex is provided in a dose of 0.005–20 mmol/kg of body weight.

9. The method of claim 5, where the fluorine-containing, macrocyclic metal complex is provided in a dose of 0.005–20 mmol/kg of body weight.

10. The method of claim 5, wherein the temperature determination is conducted on a tissue in vivo.

11. The method of claim 5, wherein the fluorine-containing, macrocyclic metal complex as temperature sensor provides a positive temperature gradient.

12. The method of claim 5, wherein the fluorine-containing, macrocyclic metal complex as temperature sensor provides a negative temperature gradient.

13. The method of claim 5, wherein at least two fluorine-containing, macrocyclic metal complexes as temperature sensors are used to provide both a positive and negative temperature gradient.

14. A process for the production of a fluorine-containing macrocyclic metal complex having at least one metal ion of an element of atomic numbers 21–29, 42, 44 or 57–83 and a complexing agent of formula I

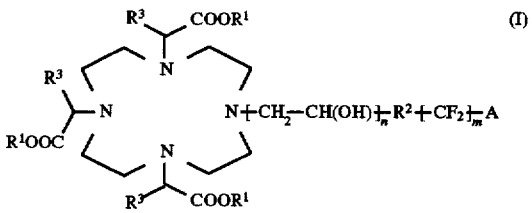

in which:
- n and m, independently of one another, stand for the numbers 0 or 1;
- $R^1$ independently of one another, stand for a hydrogen atom or a metal ion equivalent; p1 $R^3$ stands for a hydrogen atom, a straight-chain or branched $C_1$–$C_{10}$ alkyl group, which optionally is substituted by 1–5 $C_1$–$C_6$ alkoxy groups, hydroxy-$C_1$–$C_6$ alkyl groups and/or hydroxy groups; p1 $R^2$ stands for a straight-chain or branched $C_1$–$C_{10}$ alkylene group which is substituted by 1 to 3 —$CF_3$ groups and which optionally is interrupted by 1 to 5 oxygen atoms and/or carbonyl groups and/or optionally is substituted by 1 to 5 hydroxy groups, $C_1$–$C_6$-alkoxy-$C_1$–$C_6$-alkyl groups, —$OR^4$, —CO—$NR^5R^6$, —$NR^5R^6$ and/or —$NR^5$—CO—$R^6$ radicals,
  in which $R^4$ stands for a straight-chain or branched $C_1$–$C_4$ alkyl radical and $R^5$, $R^6$, independently of one another, have the meaning of $R^3$; and
- A stands for a fluorine atom wherein m is 1 or A stands for a hydrogen atom or a second macrocyclic radical of formula II,

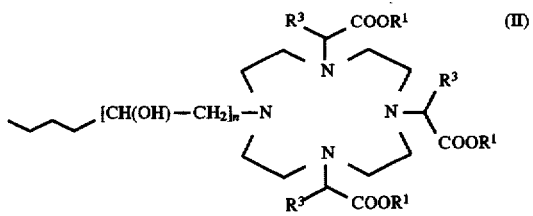

in which n, $R^1$ and $R^3$ have the indicated meanings, wherein m is 0; and salts thereof with inorganic and/or organic bases or amino acids; and $C_1$–$C_6$ alkyl or $C_6$–$C_{10}$ aryl or aralkyl esters or amides thereof; provided that at least two radicals $R^1$ stand for a metal ion equivalent;

which process comprises reacting a complexing agent of formula IV

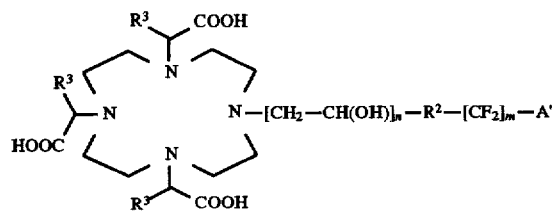

in which n, m, $R^2$ and $R^3$ have the indicated meaning and A' stands for a fluorine atom when m is 1, or A' stands for a hydrogen atom or a second macrocyclic radical of formula V,

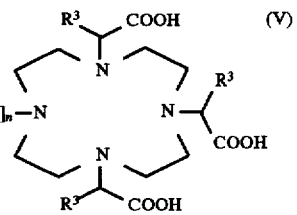

when m is 0;

with a metal salt or metal oxide of an element of atomic numbers 21–29, 42, 44 or 57–83 to produce the desired metal complexes.

15. A process for the production of the composition according to claim 6, which comprises bringing the complex dissolved in water with the additives or stabilizers usual in galenicals into a form that is suitable for enteral or parenteral administration, so that the complex is present in a concentration of 1 μm up to 1 mol/l.

* * * * *